United States Patent
Sanyal et al.

(10) Patent No.: US 12,427,199 B2
(45) Date of Patent: Sep. 30, 2025

(54) SELF-ASSEMBLED DIBLOCK COPOLYMERS COMPOSED OF PEGMEMA AND DRUG BEARING POLYMERIC SEGMENTS

(71) Applicant: RS ARASTIRMA EGITIM DANISMANLIK ILAC SANAYI TICARET ANONIM SIRKETI, Istanbul (TR)

(72) Inventors: Rana Sanyal, Istanbul (TR); Amitav Sanyal, Istanbul (TR); Sadik Kaga, Istanbul (TR)

(73) Assignee: RS ARASTIRMA EGITIM DANISMANLIK ILAC SANAYI TICARET ANONIM SIRKETI, Istanbul (TR)

( * ) Notice: Subject to any disclaimer, the term of this patent is extended or adjusted under 35 U.S.C. 154(b) by 348 days.

(21) Appl. No.: 16/349,419

(22) PCT Filed: Nov. 16, 2017

(86) PCT No.: PCT/IB2017/057155
§ 371 (c)(1),
(2) Date: May 13, 2019

(87) PCT Pub. No.: WO2018/092048
PCT Pub. Date: May 24, 2018

(65) Prior Publication Data
US 2024/0108736 A1 Apr. 4, 2024

(30) Foreign Application Priority Data
Nov. 16, 2016 (GB) ..................... 1619372

(51) Int. Cl.
| A61K 47/58 | (2017.01) |
| A61K 47/60 | (2017.01) |
| A61K 47/65 | (2017.01) |
| C08F 220/28 | (2006.01) |

(52) U.S. Cl.
CPC .............. *A61K 47/58* (2017.08); *A61K 47/60* (2017.08); *A61K 47/65* (2017.08); *C08F 220/286* (2020.02)

(58) Field of Classification Search
CPC .................................................. A61K 47/58
See application file for complete search history.

(56) References Cited

U.S. PATENT DOCUMENTS

2019/0321479 A1* 10/2019 Sanyal ................... A61K 47/58

OTHER PUBLICATIONS

Zhang et al., Chem. Mater. 28:7039-7050 (2016) (Year: 2016).*
Li L, et al. Self-assembly of random copolymers. Chem Commun (Camb). Nov. 14, 2014;50(88):13417-32.
Shao Y, et al. Block and random copolymers bearing cholic acid and oligo(ethylene glycol) pendant groups: aggregation, thermosensitivity, and drug loading. Biomacromolecules. May 12, 2014;15(5):1837-44. doi: 10.1021/bm5002262. Epub Apr. 24, 2014.
Kuperkar, K. et al. Amphiphilic Block Copolymers: Their Structures, and Self-Assembly to Polymeric Micelles and Polymersomes as Drug Delivery Vehicles. Polymers 2022, 14, 4702. https://doi.org/10.3390/polym14214702.
Horacio Cabral, et al., Block Copolymer Micelles in Nanomedicine Applications, Chemical Reviews 2018 118 (14), 6844-6892, DOI: 10.1021/acs.chemrev.8b00199.

* cited by examiner

*Primary Examiner* — Rei Tsang Shiao
(74) *Attorney, Agent, or Firm* — Lisa Mueller; Casimir Jones SC (57) ABSTRACT

This invention relates to polymer drug conjugates according to formula I, and their use for treatment of diseases such as cancer.

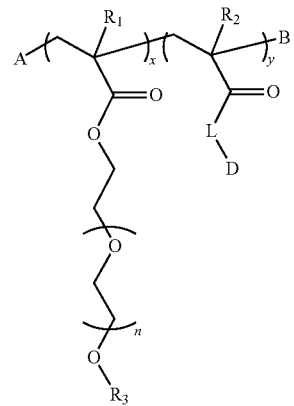

Formula I

14 Claims, 4 Drawing Sheets
Specification includes a Sequence Listing.

```
SEQUENCE LISTING

<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Gly Phe Leu Gly
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Ala Leu Ala Leu
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide, Cyclic

<400> SEQUENCE: 3

Arg Gly Asp Phe Lys
1               5
```

SELF-ASSEMBLED DIBLOCK COPOLYMERS COMPOSED OF PEGMEMA AND DRUG BEARING POLYMERIC SEGMENTS

SEQUENCE LISTING

The instant application contains a Sequence Listing which has been submitted in ASCII format via EFS-Web and is hereby incorporated by reference in its entirety. Said ASCII copy, created on May 13, 2019, is named RSGB02PCT-seq1-000001.txt and is 798 bytes in size.

FIELD OF THE INVENTION

This invention relates to polymer drug conjugates according to formula I, assemblies made up of polymer drug conjugates of formula I, methods of preparing said polymer-drug conjugates and assemblies and their use for treatment of diseases such as cancer.

BACKGROUND OF THE INVENTION

Chemotherapy agents used for treatment of cancer are mostly cytotoxic. These agents may accumulate in the tissues of the body in addition to the targeted area, which in turn causes lowered therapeutic benefit and undesired distribution of the drug throughout healthy body tissues. The uncontrolled distribution of these agents throughout the body causes severe side effects to the patient.

In order to address the abovementioned problems, drug delivery systems, which can deliver the drug to targeted areas of the body, are developed. For example in some approaches of cancer treatment, these systems make use of the enhanced permeability and retention effect (EPR) which implies that drug carriers having high molecular weight and large hydrodynamic volume accumulate in solid tumors and this, in turn leads to passive targeting of the drug molecule to the tumor tissue and minimize the damage of the chemotherapy agents to healthy tissue.

Since the discovery of the enhanced permeability and retention (EPR) effect, macromolecules with long blood circulation have become the primary substances for drug delivery due to improved accumulation in tumors through fenestrated blood vessels.

There have been great interest on polymeric assemblies in drug delivery systems for cancer disease mainly due to their body distribution properties. Present invention also relates to assemblies that are suitable for use in drug delivery, specifically anticancer agents for treatment of cancer.

TECHNICAL FIELD OF THE INVENTION

There are various types of techniques for the preparation of polymeric assemblies known in the present state of the art. For example, self-assembly of polymeric compounds is an attractive method for polymeric assembly formation. Eisenberg and coworkers demonstrated the first example of self-assembly of asymmetric copolymers in solutions in the 1990s. Then, there have been focused attention on amphiphilic block copolymers having polymer blocks with different physical and chemical properties to generate polymeric structures via self-assembly Drug loading in such polymeric assemblies can be achieved by covalent attachment or physical encapsulation via hydrophobic interactions. Considering the very low total volume of these assemblies in their colloidal suspensions, high drug loading capacity is of crucial importance to achieve effective drug formulations. Low drug loading capacity of polymeric assemblies mainly in micellar formulations is still a major drawback in the field.

Several researchers addressed this problem by taking advantage of π-π interactions through modifying the drug molecules or using an additive compound rather than providing covalent attachment. However, non-capsulated drug aggregates in the micellar type polymeric nanoparticle formulations is another drawback to provide a safe formulation for their clinical applications.

In another approach, Stenzel and co-workers have utilized drug attachable amphiphilic block copolymers to form hydrophobic segment of the block copolymers for the formation of polymeric assemblies. This strategy has the lack of complete conjugation of the drug to the polymer backbone due to steric hindrance which is resulted in not well-defined final structure. Moreover, remaining reactive groups on the polymer backbone due to incomplete conjugation may be the most important drawback of this kind of post-polymerization conjugation strategies due to possible undesirable biological interactions in vivo.

In light of the current state of the art summarized above there is need for block copolymers and assemblies formed thereof that are well defined by means of the content of the drug, that provide efficient conjugation of the drug without any remaining reactive sites and which has a high drug loading capacity.

The inventors have found that the amphiphilic block copolymers according to present invention provide formation of micellar type assemblies that has high drug content and that are well defined by means of drug attachment.

BRIEF DESCRIPTION OF THE INVENTION

Present invention relates to a polymer-drug conjugate in the form of a block co-polymer for delivery of therapeutic agents as shown in Formula I Formula I In other words, the invention relates to a polymer-drug conjugate of Formula I in the form of a block co-polymer and assemblies made from polymer-drug conjugates of Formula I, wherein Ri and $R_2$ are independently selected from H or —$CH_3$
R3 is selected from —H or —CH3
x is a natural number between 1-100
y is a natural number between 1-100
n is a natural number between 1-50 and L is a cleavable linker or L may be null and D is a therapeutic agent that is selected from a group comprising combretastatin, 5-Fluorouracil, gemcitabine, chloroquine and doxorubicine A is an end group or A may be null B is an end group or B may be null The inventors have found that in addition to overcoming the disadvantages of the prior art polymeric assemblies; the polymeric assemblies of present invention that are made up of polymer-drug conjugates of formula I also reduces the amount of polymer given to a patient due to high drug loading.

DETAILED DESCRIPTION OF THE INVENTION

The term "polymer-drug conjugate" refers to a polymeric structure having a therapeutic agent covalently attached to the polymer.

The term "polymeric assembly" refers to a structure having a diameter in between 1-100 nm. Said assemblies are made of self-assembled polymer chains and they may or may not have hollow cavities of various sizes.

The terms "polymeric backbone" and "polymer backbone" can be used interchangeably and refer to a polymer chain having side chains or pendant groups. For example, a side chain may have an oligo ethylene glycol unit and a pendant group may be bearing one therapeutic agent or any other group that can be utilized to attach a therapeutic and/or diagnostic agent or a targeting group.

Throughout the text, the term "the polymer-drug conjugate of the invention" should be construed to mean "a polymer-drug conjugate according to formula I" or "a polymer-drug conjugate of formula I" or "formula I" and these terms can be used interchangeably.

Throughout the text, the term "polymeric assemblies" should be construed to mean an "nanoparticle made up of polymer-drug conjugate of formula I" or "nanoparticle made of a copolymer as shown in formula I" or "nanoparticle that formed as a result of the self assembly of a polymer-drug conjugate of formula I" or "a micellar assembly made of a co-polymer as shown in formula I" and these terms can be used interchangeably.

The term "PEG" refers to a polyether compound having the structure of H-(0-CH2-CH2)n-OPv3, n being a natural number between 1-200 and $R_3$ selected from H or —CH3. PEG is defined as an oligomer or polymer of ethylene oxide. The terms "PEG", "polyethylene glycol", "polyethylene oxide", "PEO", "polyoxyethylene" and "POE" refer to the same structure and may be used interchangeably within this text.

In an embodiment of the invention Ri, $R_2$ and R3 are independently selected from H or —CH3

In one embodiment Ri=H, $R_2$=H, $R_3$=H or Ri=H, $R_2$=H, $R_3$=—CH$_3$ or Ri=H, $R_2$=—CH$_3$, $R_3$=H or $R_1$=H, $R_2$=—CH$_3$, $R_3$=—CH$_3$ or Ri=—CH$_3$, $R_2$=H, $R_3$=H or Ri=—CH$_3$, $R_2$=H, $R_3$=—CH$_3$ or Ri=—CH$_3$, R2=—CH$_3$, $R_3$=H or Ri=—CH$_3$, $R_2$=—CH$_3$, $R_3$=—CH$_3$.

The term "block copolymer" refers to a copolymer wherein all of one type of monomer is grouped together and the all of the other type of monomers are grouped together. The polymer-drug conjugates of the invention are in the form of block copolymer. The fact that the polymer-drug conjugates of the invention are in the form of a block copolymer allows the formation of the polymeric assembly of the invention.

The therapeutic agent is attached to the polymer via a cleavable linker so that the therapeutic agent can be released, for example, under reducing conditions, oxidizing conditions or by hydrolysis of an ester, amide, hydrazide.

Said cleavable linker can be any hydrocarbon or substituted hydrocarbon based compound which is capable of dissociating under physiological conditions. In a preferred embodiment the linker can be selected from compounds that are cleaved under the acidic conditions of the tumor (such as any C1-C10 substituted or unsubstituted and/or linear and/or cyclic hydrocarbon comprising an acetal or an ester functional group) or with the help of the overexpressed enzymes present in the intercellular or intracellular matrix of the tumor cells.

The linker can be any sort of entity capable of binding to both the polymer backbone and to the drug, such as, a poly(ethylene glycol), an amino acid, poly(amino acid) (e.g. a peptide or oligopeptide), or polypeptide (e.g. a protein), such that one end of it is capable of forming a covalent bond with the polymer backbone and the other end of it is capable of forming a covalent bond with the therapeutic agent. The linkers may also include short peptides with specific peptide sequences that are cathepsin B labile, such as Gly-Phe-Leu-Gly (SEQ ID NO: 1) also denoted as GFLG or Val-Cit or Phe-Lys or Val-Ala or Ala-Leu-Ala-Leu (SEQ ID NO: 2)

The linker can also be a C1-C10 hydrocarbon or a C1-C10 substituted or hetero substituted hydrocarbon such that it comprises a functional group that dissociates under physiological conditions, such as an acetal, ester, imine, amide, disulfide, carbonate, carbamate, hydrazone.

In an embodiment of the invention, the linker (L) is GFLG or Val-Cit or Phe-Lys or Val-Ala or Ala-Leu-Ala-Leu.

In an embodiment of the invention, the linker is a Ci-Cio hetero substituted hydrocarbon comprising at least one disulfide functional group or a Ci-Cio hetero substituted hydrocarbon comprising at least one acetal functional group or a Ci-Cio hetero substituted hydrocarbon comprising at least one ester functional group or a Ci-Cio hetero substituted hydrocarbon comprising at least one imine functional group or a Ci-Cio hetero substituted hydrocarbon comprising at least one amide functional group or a Ci-Cio hetero substituted hydrocarbon comprising at least one carbonate functional group or a Ci-Cio hetero substituted hydrocarbon comprising at least one carbamate functional group or a Ci-Cio hetero substituted hydrocarbon comprising at least one hydrazone functional group.

In another embodiment of the invention the linker may comprise a Ci-Cio substituted or hetero substituted hydrocarbon comprising two or more functional groups selected from the group comprising acetal, ester, imine, amide, disulfide, carbonate, carbamate, hydrazone.

In another embodiment of the invention the linker may be null, which means that the therapeutic agent D is attached directly to the polymer chain. The direct attachment of the therapeutic agent to the polymer chain can be through an ester, imine, amide, disulfide, carbonate, carbamate, hydrazine bond.

In a preferred embodiment of the invention the drug molecule is attached to the polymer via a direct ester bond that dissociates under physiological conditions of the tumor. In another embodiment of the invention the linker may be a combination of a Ci-Cio substituted hydrocarbon comprising at least one functional group selected from the group comprising acetal, ester, imine, amide, disulfide, carbonate, carbamate, hydrazone and a peptide chain selected from the group comprising GFLG, Val-Cit or Phe-Lys or Val-Ala or Ala-Leu-Ala-Leu. The therapeutic agent selected from combretastatin, 5-Fluorouracil, gemcitabine, chloroquine and doxorubicine can be present in an amount in between 5% to 50% by weight of the polymer-drug conjugate, preferably in an amount between 6% to 48% by weight of the drug-polymer conjugate and most preferably in an amount between 10% to 45% by weight of the drug-polymer conjugate. The therapeutic agent can be present in an amount in the range of for example; 10% to 48% or 15% to 46% or 20% to 45% or 25% to 44% by weight of the drug-polymer conjugate.

The term "end group" refers to functionalities or constitutional units that are at the extremity of a polymer. The end groups shown as A and B can be identical to or different from one another.

In an embodiment A is an end group that is optionally a fragment of a chain transfer agent or initiator or a fragment of a chain transfer agent or initiator conjugated with a targeting moiety or a fragment of a chain transfer agent or initiator having a reactive functional group.

In an embodiment B is an end group that is optionally a fragment of a chain transfer agent or initiator.

The term "chain transfer agent" refers to chemical compounds that are capable of regulating the molecular weight of polymers through interrupting the uncontrolled growth of the polymer chain. The chain transfer agents are well established in the literature and their structures are well known to those skilled in the art. The terms "chain transfer agent" and its abbreviation "CTA" refer to the same group of compounds and can be used interchangeably throughout the text.

A and B can optionally be a fragment of a chain transfer agent. Particularly when a CTA is used in the polymerization reaction, the CTA fragment may stay as an end group to the polymer. The CTA used herein, may be any material suitable for initiating the polymerization reaction known in the art. In one embodiment, A and/or B is selected from the group consisting of 3,5-Bis(2-dodecylthiocarbonothioylthio-1-oxopropoxy)benzoic acid, 3-Butenyl 2-(dodecylthiocarbonothioylthio)-2-methyl propionate, 2-Cyanobutan-2-yl 4-chloro-3,5-dimethyl-1H-pyrazole-1-carbodithioate, 2-Cyanobutanyl-2-yl 3,5-dimethyl-1H-pyrazole-1-carbodithioate, 4-Cyano-4-[(dodecylsulfanylthiocarbonyl)sulfanyl] pentanoic acid, 4-Cyano-4-[(dodecylsulfanylthiocarbonyl) sulfanyl]pentanol, Cyanomethyl (3,5-Dim ethyl-1H-pyrazol e)-carbodithioate, Cyanomethyl dodecyl trithiocarbonate, Cyanomethyl [3-(trimethoxysilyl)propyl]trithiocarbonate, 2-Cyano-2-propyl dodecyl trithiocarbonate, S,S-Dibenzyl trithiocarbonate, 2-(Dodecylthiocarbonothioylthio)-2-methylpropionic acid, 2-(Dodecylthiocarbonothioylthio)-2-methylpropionic acid 3-azido-1-propanol ester, 2-(Dodecylthiocarbonothioylthio)-2-methylpropionic acid N-hydroxysuccinimide ester, 2-(Dodecylthiocarbonothioylthio)-2-methylpropionic acid pentafluorophenyl ester, 2-(Dodecylthiocarbonothioylthio)propionic acid, Methyl 2-(dodecylthiocarbonothioylthio)-2-methylpropionate, Pentaerythritol tetrakis[2-(dodecylthiocarbonothioylthio)-2-methylpropionate], Phthalimidomethyl butyl trithiocarbonate, 1,1,1-Tris[(dodecylthiocarbonothioylthio)-2-methyl propionate]ethane, Benzyl 1H-pyrrole-1-carbodithioate, Cyanomethyl diphenylcarbamodithioate, Cyanomethyl methyl(phenyl)carbamodithioate, Cyanomethyl methyl(4-pyridyl)carbamodithioate, 2-Cyanopropan-2-yl N-methyl-N-(pyridin-4-yl)carbamodithioate, Methyl 2-[methyl (4-pyridinyl)carbamothioylthio]propionate, 1-Succinimidyl-4-cyano-4-[N-methyl-N-(4-pyridyl)carbamothioylthio]pentanoate, Benzyl benzodithioate, Cyanomethyl benzodithioate, 4-Cyano-4-(phenylcarbonothioylthio)pentanoic acid, 4-Cyano-4-(phenylcarbonothioylthio)pentanoic acid N-succinimidyl ester, 2-Cyano-2-propyl benzodithioate, 2-Cyano-2-propyl 4-cyanobenzodithioate, Ethyl 2-(4-methoxyphenylcarbonothioylthio)acetate, Ethyl 2-methyl-2-(phenylthiocarbonylthio)propionate, Ethyl 2-(phenylcarbonothioylthio)-2-phenyl acetate, Ethyl 2-(phenylcarbonothioylthio)propionate, 1-(Methoxycarbonyl)ethyl benzodithioate, 2-(4-Methoxyphenylcarbonothioylthio)ethanoic acid, 2-Nitro-5-(2-propynyloxy)benzyl 4-cyano-4-(phenylcarbonothioylthio)pentanoate 2-(Phenylcarbonothioylthio)propanoic acid, 2-Phenyl-2-propyl benzodithioate, Cyanomethyl methyl (4-pyridyl)carbamodithioate, 2-Cyanopropan-2-yl N-methyl-N-(pyridin-4-yl) carbamodithioate, Methyl 2-[methyl (4-pyridinyl) carbamothioylthio]propionate, 1-Succinimidyl-4-cyano-4-[N-methyl-N-(4-pyridyl)carbamothioylthio]pentanoate or any fragment of the initiators listed herein as itself or as conjugated with a targeting moiety before or after the polymerization reaction or as modified with a reactive group.

The term "fragment" as used herein refers to compounds that form due to breaking of one or more of the covalent bonds forming the initiator molecule.

Fragmentation of the CTAs listed herein and the structure of the formed fragments are well established in the art, thus the structure of A and B can be determined without use of inventive skills by making use of current state of the art.

A and/or B is optionally null.

In an embodiment of the invention A is null and B is a fragment of a CTA.

In another embodiment B is null and A is a fragment of a CTA.

In another embodiment A and B are both fragments of a CTA however they are structurally different from one another. In other words, A and B are different fragments of the same CTA.

In another embodiment A and B are both fragments of a CTA and they have the same chemical structure.

The term "targeting moiety" refers to molecules which has a tendency to bind to specific target sites in the body. In other words targeting moiety are molecules that bind specifically to the cell that has the complimentary receptor.

Targeting moiety can be selected from a group comprising antibodies; antibody fragments, or peptides such as Cyclo (Arg-Gly-Asp-D-Phe-Lys) (SEQ ID No: 3) (cRGDfK). In a preferred embodiment cRGDfK is used as the targeting moiety.

The term "reactive group" refers to an atom or associated group of atoms in a chemical substance that is intended or can be reasonably anticipated to undergo facile chemical reaction.

The reactive group can be an acetal, hemiacetal, carboxylic acid, alcohol, amide, imide, anhydride, aryl halide, azo compound, diazo compound, hydrazine, azide, carbonate, chlorosilane, cyanide, ester, sulfate ester, phosphate ester, thiophosphate ester, isocyanate, isothiocyanate, thiocarbamate ester, dithiocarbamate ester. Preferably the reactive group is an ester, imide or carbonate. The reactive group can for example be N-hydroxysuccinimide.

Depending on the polymerization techniques employed in preparation of the polymer conjugates of the invention A and/or B can be a fragment of an initiator.

An initiator as used herein refers to a chemical compound that reacts with a monomer to form an intermediate compound capable of linking successively with a large number of other monomers into a polymeric compound. The terms "initiator" and "polymerization initiator" can be used interchangeably within the context of this application.

Depending on the polymerization techniques used for preparing the polymer conjugates of the invention, different initiator agents can be used.

In an embodiment A and/or B is a fragment of an initiator that can be selected from the group comprising 4,4'-Azobis (4-cyanovaleric acid), 4,4'-Azobis(4-cyanovaleric acid), 1,1'-Azobis(cyclohexanecarbonitrile), 2,2'-Azobis(2-methylpropionamidine) dihydrochloride, 2,2'-Azobis(2-methylpropionitrile) (also known as AIBN), Ammonium persulfate, hydroxymethanesulfinic acid monosodium salt dihydrate, potassium persulfate, sodium persulfate, tert-Butyl hydroperoxide, tert-Butyl peracetate, Cumenehydroperoxide, 2,5-Di(tert-butyl peroxy)-2,5-dim ethyl-3-hexyne, Di cumyl peroxide, 2,5-Bis(tert-butylperoxy)-2,5-dimethylhexane, 1,1-Bis(tert-butylperoxy)-3,3,5-trimethylcyclohexane, 1,1-Bis(tert-amylperoxy)cyclohexane, Benzoyl peroxide, 2-Butanone peroxide, tert-Butyl peroxide, Di-tert-amyl peroxide, Lauroyl peroxide, tert-Butyl peroxybenzoate, tert-Butylperoxy 2-ethylhexyl carbonate, tert-Butyl hydroperoxide, 2-Azidoethyl 2-bromoisobutyrate, Bis[2-(2-bromoisobutyryloxy)undecyl]disulfide, Bis[2-(2'-bromoisobutyryloxy) ethyl]disulfide, 2-Bromoisobutanoic acid N-hydroxysuccinimide ester, 2-Bromoisobutyric anhydride, a-Bromoisobutyryl bromide, 2-(2-Bromoisobutyryloxy) ethyl methacrylate, tert-Butyl a-bromoisobutyrate, 3-Butynyl 2-bromoisobutyrate, Dipentaerythritolhexakis(2-bromoisobutyrate), Dodecyl 2-bromoisobutyrate, Ethyl a-bromoisobutyrate, Ethylene bis(2-bromoisobutyrate), 2-Hydroxyethyl 2-bromoisobutyrate, 1-(DL-1,2-Isopropylideneglyceryl) 2-bromoisobutyrate, Methyl a-bromoisobutyrate, Octadecyl 2-bromoisobutyrate, Pentaerythritoltetrakis(2-bromoisobutyrate), 1-(Phthalimidomethyl) 2-bromoisobutyrate, Poly(ethylene glycol) bis(2-bromoisobutyrate), Propargyl 2-bromoisobutyrate, 1,1,1-Tris (2-bromoisobutyryloxymethyl)ethane, 1 O-Undec enyl 2-bromoisobutyrate, N-tert-Butyl-O-[1-[4-(chloromethyl) phenyl]ethyl]-N-(2-methyl-1-phenyl propyl)hydroxyl amine, N-tert-Butyl-N-(2-methyl-1-phenyl propyl)-O-(1-phenyl ethyl)hydroxyl amine, TEMPO, TEMPO methacrylate, 2,2,5-Trimethyl-4-phenyl-3-azahexane-3-nitroxide, 3,5-Bis(2-dodecylthiocarbonothioylthio-1-oxopropoxy) benzoic acid, 3-Butenyl 2-(dodecylthiocarbonothioylthio)-2-methylpropionate, 4-Cyano-4-[(dodecylsulfanylthiocarbonyl)sulfanyl]pentanoic acid, 4-Cyano-4-[(dodecylsulfanylthiocarbonyl)sulfanyl]pentanol, Cyanomethyl dodecyl, Cyanomethyl [3-(trimethoxysilyl) propyl]trithiocarbonate, 2-Cyano-2-propyl dodecyl trithiocarbonate, S,S-Dibenzyl trithiocarbonate, 2-(Dodecylthiocarbonothioylthio)-2-methylpropionic acid, 2-(Dodecylthiocarbonothioylthio)-2-methylpropionic acid, 3-azido-1-propanol ester, 2-(Dodecylthiocarbonothioylthio)-2-methylpropionic acid N-hydroxysuccinimide ester, 2-(Dodecylthiocarbonothioylthio)-2-methylpropionic acid pentafluorophenyl ester, 2-(Dodecylthiocarbonothioylthio) propionic acid, Methyl 2-(dodecylthiocarbonothioylthio)-2-methylpropionate, Pentaerythritol tetrakis[2-(dodecylthiocarbonothioylthio)-2-methylpropionate], Phthalimidomethyl butyl trithiocarbonate, 1,1,1-Tris[(dodecylthiocarbonothioylthio)-2-methylpropionate]ethane, benzyl benzodithioate, Cyanomethyl benzodithioate, 4-Cyano-4-(phenylcarbonothioylthio)pentanoic acid, 4-Cyano-4-(phenylcarbonothioylthio)pentanoic acid N-succinimidyl ester, 2-Cyano-2-propyl benzodithioate, 2-Cyano-2-propyl 4-cyanobenzodithioate, Ethyl 2-(4-methoxyphenylcarbonothioylthio)acetate, Ethyl 2-methyl-2-(phenylthiocarbonylthio)propionate, Ethyl 2-(phenylcarbonothioylthio)-2-phenyl acetate, Ethyl 2-(phenylcarbonothioylthio)propionate, 1-(Methoxycarbonyl) ethyl benzodithioate, 2-(4-Methoxyphenylcarbonothioylthio)ethanoic acid, 2-Nitro-5-(2-propynyloxy)benzyl, 4-cyano-4-(phenylcarbonothioylthio)pentanoate, 2-(Phenylcarbonothioylthio)propanoic acid, 2-Phenyl-2-propyl benzodithioate, Cyanomethyl methyl(4-pyridyl)carbamodithioate, Cyanopropan-2-yl N-methyl-N-(pyridin-4-yl) carbamodithioate, Methyl 2-[methyl(4-pyridinyl) carbamothioylthio]propionate, 1-Succinimidyl-4-cyano-4-[N-methyl-N-(4-pyridyl)carbamothioylthio]pentanoate or a combination thereof as itself or as conjugated with a targeting moiety before or after the polymerization reaction or as modified with a reactive group.

The definition and examples of targeting moiety are as described above.

The definition and examples of the reactive group are as described above.

The chain transfer agents and the initiators listed within this application are given as example for illustration of the invention, any chemical compound published before or after the filing of this document that can act as a CTA and/or initiator are included within the scope of the invention.

The measurement of the amount of drug in the polymer conjugate of the invention is made by using conventional techniques well-known in the art, for example by calculation of the drug ratio from a $^1$H-NMR of the polymer-drug conjugate or by determination of the amount by forced release of the drug.

In another embodiment the polymer-drug conjugate of the invention has an average molecular weight in between 5 kDa to 60 kDa. In a preferred embodiment the polymer-drug conjugate of the invention has an average molecular weight in between, 6 Da to 50 kDa and in a most preferred embodiment the polymer-drug conjugate of the invention has an average molecular weight in between 7 kDa to 40 kDa.

Molecular weight of the polymer-drug conjugate of the invention is determined by using conventional techniques known in the art for example by using gel permeation chromatography (GPC).

Another embodiment of the invention is polymeric assemblies formed with polymer-drug conjugates shown with formula I wherein;

Formula I $R_1$ and $R_2$ are independently selected from H or —$CH_3$
$R_3$ is selected from —H or —$CH_3$ x is a natural number between 1-100
y is a natural number between 1-100
n is a natural number between 1-50 and
L is a cleavable linker or L may be null and
D is a therapeutic agent that is combretastatin or 5-Fluorouracil or gemcitabine or chloroquine or doxorubicine
A is an end group or A may be null
B is an end group or B may be null Another embodiment of the invention is polymeric micelles formed with polymer-drug conjugates shown with formula I wherein;

Formula I

Ri and $R_2$ are independently selected from H or —$CH_3$
R3 is selected from —H or —CH3
x is a natural number between 1-100
y is a natural number between 1-100
n is a natural number between 1-50 and
L is a cleavable linker or L may be null and
D is a therapeutic agent that is combretastatin or 5-Fluorouracil or gemcitabine or chloroquine or doxorubicine
A is an end group or A may be null
B is an end group or B may be null In another embodiment, assemblies according to present invention are used to encapsulate therapeutic molecules, in that sense polymeric assemblies made up of polymer-drug conjugates of formula I encapsulating therapeutic agents other than those attached to the polymer chain are another embodiment of this invention.

The term "encapsulating" refers to confinement of a guest molecule, for example a therapeutic agent inside the cavity of a host molecule, for example a polymeric assembly made up of the polymer-drug conjugate of formula I. The encapsulation preferably takes place through non-covalent interactions of the therapeutic molecule with the polymeric assembly of the invention.

The term "therapeutic agent" refers to any compound that is suitable for use in treatment of a disease. The terms "therapeutic agent", "chemotherapy agent", "anticancer agent" and "antineoplastic agent" all refer to the compounds suitable for use in treatment of a disease and these terms can be used interchangeably. In one embodiment, the disease is cancer.

Additionally, a "therapeutic agent" also refers to any agent that is suitable for use in treating of a disease, for example cancer. Any therapeutic agent which can be directly or indirectly attached to the polymer-drug conjugate of the invention can be used. U.S. Pat. No. 6,342,221 also describe agents related to anticancer agents and this document is incorporated herein by reference. Anticancer agents can be classified as but are not limited to, chemotherapeutic agents, cytotoxins, antimetabolites, alkylating agents, protein kinase inhibitors, anthracyclines, antibiotics, antimitotic agents (e.g. antitubulin agents), corticosteroids, radiopharmaceuticals, and proteins (e.g. cytokines, enzymes, or interferons). Specific examples of anticancer agents are for example, docetaxel, gemcitabine, imatinib, 5-fluorouracil, 9-aminocamptothecin, amine-modified geldanamycin, doxorubicin, paclitaxel, procarbazine, hydroxyurea, mesoe-chlorin, cisplatin and radionuclides (e.g 1-131, Y-90, In-111, and Tc-99m). There are many other anticancer agents known in the art and many continue to be developed, those agents are also included within the scope of this invention.

The therapeutic agent can also be selected from a sub group comprising, but not limited to, nucleoside analogs, antifolates, other metabolites, topoisomerase I inhibitors, anthracyclines, podophyllotoxins, taxanes, vinca alkaloids, alkylating agents, platinates, antihormones, radiopharmaceutics, monoclonal antibodies, tyrosine kinase inhibitors, mammalian target of rapamycin (mTOR) inhibitors, retinoids, immunomodulatory agents, histonedeacetylase inhibitors and other agents.

Nucleoside analogs can be selected from a group comprising, but not limited to, azacitidine, cladribine, clofarabine, cytarabine, decitabine, floxuridine, fludarabine, gemcitabine, mercaptopurine, nelarabine, pentostatin, tioguanine, trifluridine, tipiracil.

Antifolates can be selected from a group comprising, but not limited to, methotrexate, pemetrexed, pralatrexed, raltitrexed.

Other metabolites can be selected from a group comprising, but not limited to, hydroxycarbamide.

Topoisomerase I inhibitors can be selected from a group comprising, but not limited to, irinotecan and topotecan.

Anthracyclines can be selected from a group comprising, but not limited to, daunorubicin, doxorubicin, epirubicin, idarubicin, mitoxantrone, valrubicin.

Podophyllotoxins can be selected from a group comprising, but not limited to, etoposide and teniposide.

Taxanes can be selected from a group comprising, but not limited to, cabazitaxel, docetaxel, paclitaxel.

*Vinca* alkaloids can be selected from a group comprising, but not limited to, vinblastine, vincristine, vindesine, vinflunine, vinorelbine.

Alkylating agents can be selected from a group comprising, but not limited to, bendamustine, chlorambucil, dacarbazine, melphalan, streptozotocin, trabectedin.

Antihormone compounds can be selected from a group comprising, but not limited to, abiraterone, bicalutamide, cyproterone, degarelix, exemestane, fulvestrant, goserelin, histrelin, leuprolide, mifepristone, triptorelin.

Tyrosine kinase inhibitors can be selected from a group comprising, but not limited to, afatinib, axitinib, bosutinib, cobimetinib, crizotinib, dasatinib, erlotinib, gefitinib, imatinib, lapatinib, nilotinib, osimertinib, pazopanib, ruxolitinib, sunitinib, vandetanib.

Mammalian target of rapamycin (mTOR) inhibitors can be selected from a group comprising, but not limited to everolimus, temsirolimus.

Retinoids can be selected from a group comprising, but not limited to, alitretinoin, bexarotene, isotretinoin, tamibarotene, tretinoin.

Immunomodulatory agents can be selected from a group comprising, but not limited to, lenalidomide, pomalidomide, thalidomide.

Histone deacetylase inhibitors can be selected from a group comprising, but not limited to, belinostat, panobinostat, valproate, vorinostat.

Platinates can be selected from a group comprising, but not limited to, cisplatin, carboplatin, oxaliplatin, nedaplatin.

Other agents can be selected from a group comprising, but not limited to, anagrelide, ceritinib, dabrafenib, idelalisib, ibrutinib, palbociclib, vemurafenib, bleomycin, bortezomib, dactinomycin, eribulin, estramustine, ixabepilone, mitomycin, procarbazine, alectinib, fluxymesterone, iobenguane, imiguimod, interferon, ixazomib, lanreotide, lentinan, octreotide, omacetaxine, tegafur, gimerazil, oteracil, uracil, combretastatin, chloroquine.

In a preferred embodiment of the invention the therapeutic agent is selected from taxanes, antifolates, tyrosine kinase inhibitors, anthracyclines, nucleoside analogs or other agents. Most preferably the therapeutic agent is selected from a group comprising docetaxel, pemetrexed, chloroquine, combretastatin, gemcitabine, doxorubicine, Fluorouracil (5-FU), 5'-Deoxy 5-Fluorocytidine (5'-DFCR), lapatinib.

In an embodiment of the invention the therapeutic agent is docetaxel.

In an embodiment of the invention the therapeutic agent is carboplatin.

In an embodiment of the invention the therapeutic agent is doxorubicine.

Another embodiment of the invention is a method (Method I) for preparation of the polymer-drug conjugate of the invention (formula I) which comprises (i) polymerization of PEG (meth)acrylate monomer (formula II)

Formula II wherein
R1 is selected from H or —CH3
R3 is selected from —H or —CH3
n is a natural number between 1-50 to give a polymer of formula IIa

Formula IIa wherein
A is an end group or A may be null
B is an end group or B may be null
And then (ii) further reacting formula IIa with a (meth)acrylate-L-D monomer (Formula IIIa)

Formula IIIa wherein $R_2$ is selected from H or —CH3
L is a cleavable linker or L may be null
D is a therapeutic agent selected from a group comprising combretastatin, 5-FU, gemcitabine, chloroquine, doxorubicine to give polymer-drug conjugate of formula I.

In another aspect, a method (Method II) for preparation of the polymer-drug conjugate of the invention (formula I) comprises (i) polymerization of PEG (meth)acrylate monomer (Formula II)

Formula II wherein
R1 is selected from H or —CH3
R3 is selected from —H or —CH3
n is a natural number between 1-50
to give a polymer of formula IIa

Formula IIa wherein
A is an end group or A may be null
B is an end group or B may be null
And then (ii) further reacting formula IIa with a (meth)acrylate-L monomer (Formula IIIb)

Formula IIIb wherein $R_2$ is selected from H or —CH3
L is a cleavable linker or L may be null and
To give a copolymer as shown in formula IIb Formula IIb wherein x is a natural number between 1-100 and
y is a natural number between 1-100
and then (iii) reacting formula IIb with a therapeutic agent (D) selected from a group comprising combretastatin, 5-FU, gemcitabine, chloroquine, doxorubicine to give polymer conjugate shown in formula I.

Another embodiment of the invention is a method (Method III) for preparation of the polymer-drug conjugate of the invention (formula I) which comprises (i) polymerization of PEG (meth)acrylate monomer (Formula II)

Formula II wherein
R1 is selected from H or —CH3
R3 is selected from —H or —CH3
n is a natural number between 1-50
to give a polymer of formula IIa Formula IIa wherein
A is an end group or A may be null
B is an end group or B may be null
And then (ii) further reacting formula IIa with a (meth)acrylate-L-D monomer (Formula IIIa)

Formula IIIa wherein R$_2$ is selected from H or —CH3

L is a cleavable linker or L may be null

D is a therapeutic agent selected from a group comprising combretastatin, 5-FU, gemcitabine, chloroquine, doxorubicine to give a block copolymer And then (iii) reacting formed block co-polymer with a targeting moiety to give a polymer-drug conjugate shown in formula I.

The term "acrylate" refers to derivatives of acrylic acids. These derivatives include the parent acid (CH$_2$CHCO$_2$H) and esters, thus the term "acrylate based" defines functional groups having any of the abovementioned acrylate derivatives.

The term "methacrylate" refers to derivatives of methacrylic acids. These derivatives include the parent acid (CH$_2$C(CH$_3$)CO$_2$H) and esters. Thus the term "methacrylate based" defines functional groups having any of the above-mentioned methacrylate derivatives.

The term "(meth)acrylate" refers to the terms "acrylate" and "methacrylate". Thus, the term "(meth)acrylate" can be used interchangeably with "acrylate" and "methacrylate" and comprises all features of these terms as described above. The term "(meth)acrylate" should be construed to mean "methacrylate and/or acrylate"

Step (i) of methods I, II and III may further comprise use of a chain transfer agent and/or an initiator.

In another aspect, the invention relates to polymer-drug conjugate of formula I prepared by any one of the methods I, II or III.

In another embodiment, invention relates to polymer-drug conjugates of formula I prepared by method I as this method provides a polymer-drug conjugate with a highly well defined polymer structure and drug content. Also, polymer-drug conjugates prepared with this method do not have free reactive groups on the side chain which remain unconjugated to a drug molecule.

In one embodiment, PEG (meth)acrylate (Formula II) is preferably selected from a group comprising; polyethylene glycol methyl ether methacrylate (CAS No: 26915-72-0), polyethylene glycol methacrylate (CAS No: 25736-86-1), polyethylene glycol methyl ether acrylate (CAS No: 32171-39-4), and poly ethylene glycol acrylate (CAS No: 9051-31-4), see table 1 for structures of the compounds. In a preferred embodiment of the invention, polyethylene glycol methyl ether methacrylate, wherein R$_1$ and R$_3$ are both-CH$_3$, is used.

In an embodiment of the invention PEG (meth) acrylate (Formula II) has an average molecular weight in between 50-2000 g/mol is used. In a preferred embodiment PEG (meth)acrylate (Formula II) has an average molecular weight in between 100-1500 g/mol and in a most preferred embodiment PEG (meth)acrylate (Formula II) has an average molecular weight in between 150-1000 g/mol. PEG (meth)acrylate (Formula II) of the invention can have an average molecular weight of for example 60, 70, 80, 80, 100, 150, 200, to 250, 300, 400, 500, 600, 700, 800, 900, 1000 g/mol.

The cleavable linker according to present invention can be obtained from commercial sources or may be prepared according to known methods provided in literature.

In another aspect, present invention relates to a block copolymer of formula IIb for use in synthesis of polymer drug conjugate of formula I Formula IIb wherein;
x is a natural number between 1-100,
y is a natural number between 1-100,
R$_1$ and R$_2$ are independently selected from H or —CH$_3$,
R$_3$ is selected from —H or —CH$_3$,
n is a natural number between 1-50 and,
L is a cleavable linker or L may be null
A is an end group or A may be null
B is an end group or B may be null.

As disclosed above, methods for preparing the polymer drug conjugate of formula I (Method I, II and III) comprise at least two polymerization steps, wherein monomers formula II and monomers of formula IIIa or IIIb are polymerized. In an embodiment of the invention, these polymerization steps may further comprise an initiator and/or a polymerization agent and/or a solvent.

The polymer-drug conjugate of the invention can be prepared by any of the known polymerization methods. Any suitable initiators and/or catalysts known in the art can be used for the preparation of the polymer-drug conjugate of the present invention. Where a polymerization initiator is used, the initiator or a fragment thereof may be present in the resulting polymer-drug conjugate.

The polymer backbone of the polymer-drug conjugate of the invention can be obtained by for example bulk polymerization, solution polymerization and/or suspension polymerization techniques known in the art.

The polymerization technique used for the preparation of the polymer-drug conjugate of the present invention may propagate through free-radical polymerization or controlled/living free radical polymerization. Herein the term "controlled/living free radical polymerization" refers to atom transfer radical polymerization (ATRP), Reversible addition fragmentation chain transfer (RAFT) polymerization, iodine transfer polymerization (ITP), selenium centered radical mediated polymerization, telluride mediated polymerization (TERP), nitroxide mediated polymerization (NMP). In a preferred embodiment of the invention RAFT polymerization is used to prepare the polymer-drug conjugates of the invention.

A suitable polymerization initiator can be selected from the group given in this document.

In case of employing RAFT polymerization a CTA and an initiator can be used together for preparing the polymer drug conjugates of the invention according to the Methods I, II or III provided herein.

In an embodiment of the invention the polymer-drug conjugate of the invention and polymeric assemblies made from them can further comprise targeting groups. Herein the term "targeting group" refers to tumor specific ligands that bind specifically to the cell, preferably the tumor cell that has a complimentary receptor.

The term "targeting group" means a molecule which serves to deliver the polymer-drug conjugate of the invention to a specific site for the desired activity, i.e. it provides localization of the compound. The localization is mediated by specific recognition of molecular determinants, molecular size of the targeting agent or conjugate, ionic interactions, hydrophobic interactions, and the like. Other mechanisms of targeting an agent to a particular tissue or region are known to those of skill in the art. Targeting ligands include, for example, molecules that bind to molecules on a targeted cell surface. Exemplary targeting ligands include antibodies, antibody fragments, small organic molecules, peptides, peptoids, proteins, polypeptides, oligosaccharides, transferrin, HS-glycoprotein, coagulation factors, serum proteins, beta-glycoprotein, G-CSF, GM-CSF, M-CSF, EPO, and the like. In exemplary embodiments of the present invention, the targeting system includes covalently attaching a targeting ligand such as RGDf, EPPT1 peptide, bisphosphonic acid or folate to the carrier molecule or linker.

In certain embodiments, the present invention is characterized by polymer-drug conjugates with or without a targeting ligand. In some embodiments the targeting ligand can be RGDfK, EPPT1, bisphosphonic acid or folate.

Another embodiment of the present invention provides a method for delivering a therapeutic agent, comprising administering to a subject an effective amount of polymer-drug conjugate shown with formula I.

Another embodiment of the present invention provides a method for delivering a therapeutic agent, comprising administering to a subject an effective amount of a polymeric assembly made up of polymer-drug conjugate shown with formula I.

Another embodiment of the invention is the polymer-drug conjugate of the invention for use in treatment of a variety of disorders that require the delivery of anticancer or similar agents.

Another embodiment of the invention is the polymeric assemblies made up of polymer-drug conjugates of the invention for use in treatment of a variety of disorders that require the delivery of anticancer or similar agents.

In a preferred embodiment, the invention is related to a polymer-drug conjugate shown with formula I for use as a medicament for treatment of cancer.

In a yet another preferred embodiment, the invention is related to a polymeric assembly made up of polymer-drug conjugate of formula I for use as a medicament for treatment of cancer.

As used herein, "treat" or "treating" means to inhibit, reduce, modulate, ameliorate, or block at least one symptom that characterizes a pathologic condition, in a subject threatened by, or afflicted with, the condition. A non-limiting list of different types of cancers is as follows: carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumours, myelomas, metastatic cancers, or cancers in general. Specific examples of of cancers that the disclosed compositions can be used to treat include B cell lymphoma, T cell lymphoma, mycosis fungoides, Hodgkin's Disease, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

Polymer-drug conjugates of invention and/or polymeric assemblies made up of the polymer-drug conjugates of the invention may also be used for the treatment of precancer conditions such as cervical and anal dysplasias, other dysplasias, severe dysplasias, hyperplasias, atypical hyperplasias, and neoplasias.

The terms "cancer" and "cancerous" as used herein refers to malignant tumors or describe the physiological condition characterized by unregulated cell growth.

As discussed herein, polymer-drug conjugates of invention and/or polymeric assemblies made up of the polymer-drug conjugates of the present invention find use in the treatment and/or prophylaxis of cancer. For such use the polymer-drug conjugate of invention and/or polymeric assemblies made up of the polymer-drug conjugates of the present invention will generally be administered in the form of a pharmaceutical composition.

Thus, according to the invention there is provided a pharmaceutical composition comprising a polymer-drug conjugate according to formula I and at least one pharmaceutically acceptable diluent, excipient and/or carrier. The term "treatment" includes either therapeutic or prophylactic therapy.

Moreover, according to the invention there is provided a pharmaceutical composition comprising a polymeric assembly made up of a polymer-drug conjugate according to formula I and at least one pharmaceutically acceptable diluent, excipient and/or carrier.

The composition comprising the polymer-drug conjugate of the invention and/or polymeric assemblies made up of the polymer-drug conjugates of the present invention may be in any suitable form depending upon the desired method of administering it to a patient. The composition comprising polymer drug conjugates of the invention and/or polymeric assemblies made up of the polymer-drug conjugates of the invention can be formulated to be administered orally, e.g. in the form of liquid dispersions or aqueous or oily suspensions or they can formulated for parenteral administration, for example for subcutaneous, intravenous, intramuscular, intrasternal, intraperitoneal, intradermal, transdermal or other infusion techniques. The composition comprising the polymer drug conjugates of the invention and/or polymeric assemblies made up of the polymer-drug conjugates of the present invention can also be formulated for administration by inhalation in form of an aerosol or solution for administration with and inhaler or nebulizer. The polymer-drug conjugates of the invention and/or polymeric assemblies made up of the polymer-drug conjugates of the invention are preferably administered to a subject transdermally, subcutaneously, intranasally, intravenously, intramuscularly, intratumorally or via inhalation. The most suitable route for administration in any given case will depend on the particular therapeutic agent present in the polymer-drug conjugate of the present invention, the subject, and the nature and severity of the disease and the physical condition of the subject.

The polymer-drug conjugates of the invention and/or polymeric assemblies made up of the polymer-drug conjugates of the invention may be administered in combination, e.g. simultaneously, sequentially or separately, with one or more other therapeutically active compounds, which may be an anti-cancer agent or it is an immunomodulatory, antiviral, antiinfective, antimicrobial, antiinfective or anesthetic agent or combinations thereof.

Polymeric assemblies of the invention may be encapsulating a second therapeutic agent selected from the list provided above and additionally may further be administered in combination, e.g. simultaneously, sequentially or separately, with one or more other therapeutically active compounds, which may be an anti-cancer agent or it is an immunomodulatory, antiviral, antiinfective, antimicrobial, antiinfective or anesthetic agent or combinations thereof.

Said second therapeutic agent can be selected from the therapeutic agents listed above on the condition that it is different from the one present in the polymer-drug conjugate of the invention.

Comprising in the context of the present specification is intended to meaning including.

Where technically appropriate, embodiments of the invention may be combined.

Embodiments are described herein as comprising certain features/elements. The disclosure also extends to separate embodiments consisting or consisting essentially of said features/elements.

Technical references such as patents and applications are incorporated herein by reference.

Any embodiments specifically and explicitly recited herein may form the basis of a disclaimer either alone or in combination with one or more further embodiments.

The invention will now be described with reference to the following examples, which are merely illustrative and should not in any way be construed as limiting the scope of the present invention.

EXAMPLES

Below examples provide step-by-step preparation of the polymer-drug conjugates of formula I and polymeric assemblies thereof.

Example 1A: Synthesis of Polymerizable Combretastatin-A4 Monomer (Comb MA)

Combretastatin-A4 (300 mg, 0.95 mmol), triethyl amine (TEA, 191 mg, 1.89 mmol), methacryloyl chloride (198 mg, 1.89 mmol) were dissolved in dry dichloromethane (DCM, 10 mL) under $N_2$ in a 25 mL round bottom flask. Reaction was stirred for 16 h at room temperature. The crude was extracted with saturated NaHCO3 (20 mL×2) and distilled water (20 mL×2). Organic layer was dried with Na2SO4 and the solvent was evaporated. The CombMA monomer was purified using column chromatography on silica with hexanes.

Example IB: Preparation of Chain Transfer Agent (CTA) Having a Reactive Functional Group 4-cyanopentanoic acid dithiopentanoate (CPDB) is a CTA and this CTA was modified with N-hydroxysuccinimide (NETS) which is a reactive functional group in accordance with the below procedure;

Briefly, CPADB (200 mg, 0.72 mmol) and N-hydroxysuccinimide (125 mg, 1.07 mmol) were dissolved in anhydrous DCM (4 mL). Dicyclohexylcarbodiimide (DCC) (177 mg, 0.86 mmol) was dissolved in anhydrous DCM (1 mL). Two solution mixtures were then mixed and the reaction mixture was stirred at room temperature in the dark for 16 h. The insoluble white byproduct dicyclohexylurea (DCU) was removed by filtration. Obtained solution was dried under vacuo and the crude product was purified by column chromatography on silica with hexane and EtOAc.

Example 1C: Synthesis of POEGMEMA and NHS-POEGMEMA Homopolymers

Reversible addition-fragmentation chain transfer (RAFT) polymerization was used for the synthesis of POEGMEMA and NHS activated POEGMEMA (NHS-POEGMEMA) homopolymers. For the synthesis of POEGMEMA polymer, to a solution of OEGMA (600 mg, 2.0 mmol) and CPADB (20.12 mg, 0.072 mmol) in DMF (3 mL), was added AIBN (1.31 mg, 0.008 mmol). The mixture was purged with $N_2$ to remove 02 and polymerization was stirred for at 70° C. Polymerization was stopped by cooling and air exposure. POEGMEMA polymer was purified by precipitation in diethyl ether. The polymer precipitate was dried under vacuo to give approximately 35 OEGMEMA repeating units (460 mg, 77% yield). For the synthesis of NHS-POEGMEMA homopolymer same procedure was applied using SCPDB (27.10 mg, 0.072 mmol) as chain transfer agent to give approximately 35 OEGMEMA repeating units (480 mg, 80% yield)

Example ID: Synthesis of POEGMEMA-Co-CombMA and NHS-POEGMEMA-Co-CombMA Block Copolymers RAFT polymerization was used for the synthesis of POEGMEMA-b-PCombMA and NHS-POEGMEMA-b-PCombMA block copolymers. To a solution of CombMA (100 mg, 0.26 mmol) and POEGMEMA polymer as macro chain transfer agent (50 mg, 0.005 mmol) in DMF (0.75 mL), was added AIBN (0.15 mg, 0.00092 mmol). The mixture was purged with $N_2$ to remove $O_2$ and polymerization was stirred at 65° C. Polymerization was stopped by cooling and air exposure. The crude was precipitated in diethyl ether. The polymer precipitate was dried under vacuo to give approximately 32 CombMA repeating units (98 mg, 65% yield). Same procedure was applied for the synthesis of NHS-POEGMEMA-b-PCombMA block copolymer using NHS-POEGMEMA (50 mg, 0.005 mmol) as macro chain transfer agent to give approximately 33 CombMA repeating units (105 mg, 70% yield).

Example IE: Synthesis of Targeted Block Copolymer

Figure 1:
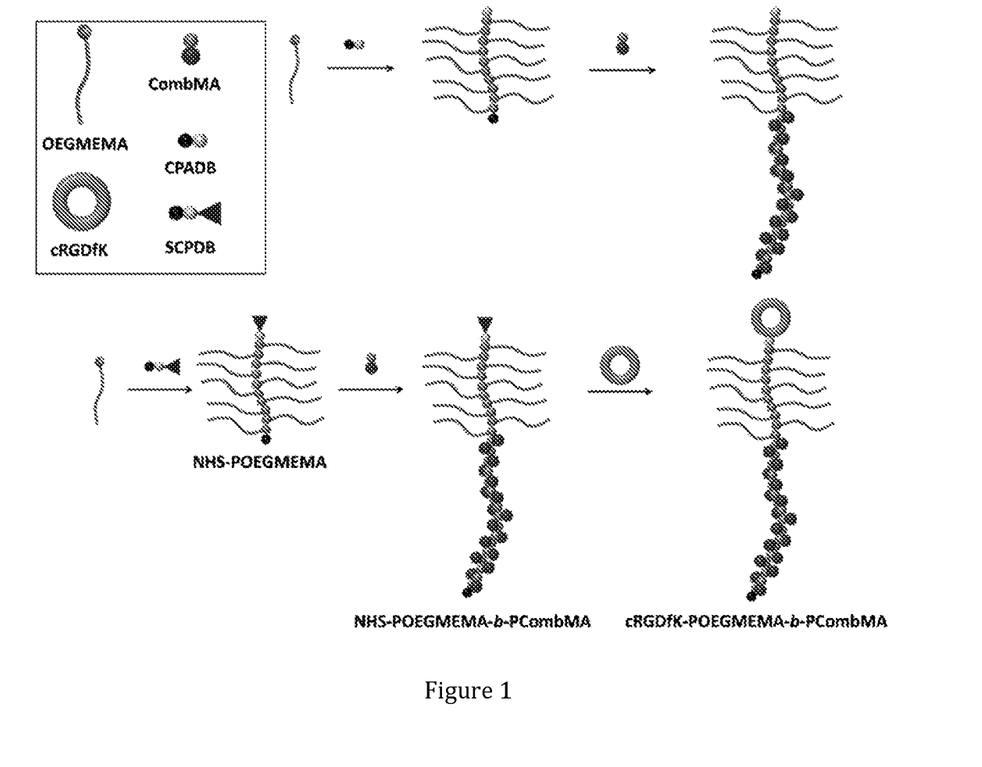
FIG. 1: Schematic representation showing synthesis of NHS-modified polymer-drug conjugate (polymer drug conjugate of formula I having a reactive functional group) and cRGDf modified polymer-drug conjugate (polymer drug conjugate of formula I having a targeting group)

NHS-POEGMEMA-b-PCombMA (50 mg, 0.002 mmol) and cRGDfK (6.4 mg, 0.01 mmol) were co-dissolved in DMF (0.25 mL) and NN-Diisopropylethylamine (6.5 mg, 0.05 mmol) was added to this reaction mixture. The reaction mixture was stirred at 30° C. for 24 h. The crude was precipitated in diethyl ether. The polymer precipitate was dried under reduced pressure to give cRGDfK-POEG-MEMA-b-CombMA (41 mg, 82% yield). An overall scheme showing the preparation of the cRGDf-POEGMEMA-b-CombMA Block Copolymer is provided as FIG. 1.

Example IF: Preparation of Targeted and Non-Targeted Polymeric Assemblies

Herein "targeted" refers to polymeric assemblies made up of cRGDf-POEGMEMA-b-CombMA block copolymers and "non-targeted" refers to polymeric assemblies made up of POEGMEMA-b-PCombMA block copolymers.

Figure 2:
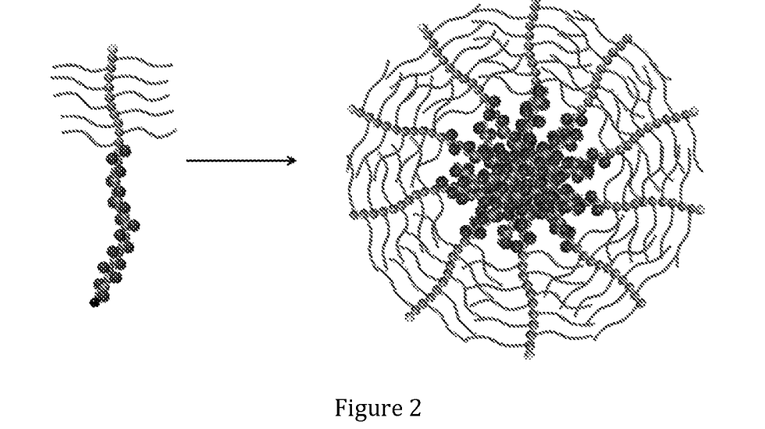
FIG. 2: Schematic representation showing preparation of non-targeted polymeric assemblies of invention from polymer drug conjugates of formula I.
Figure 3:
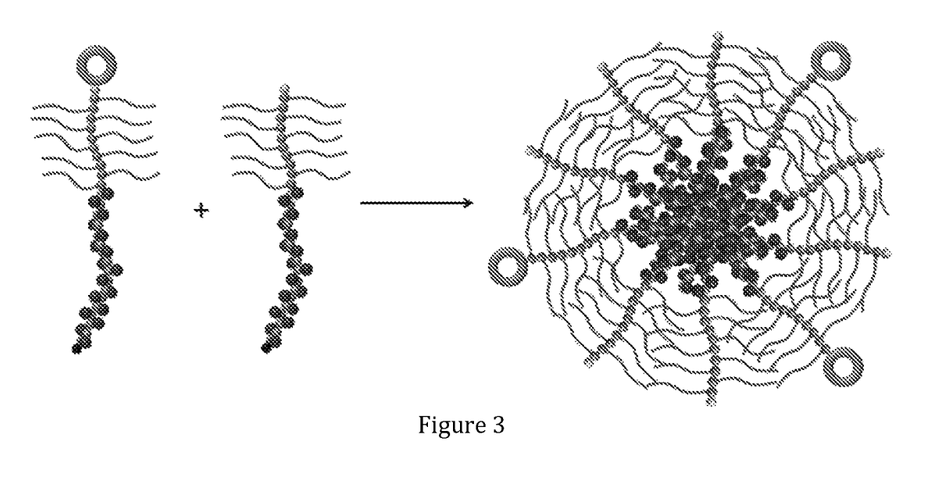
FIG. 3: Schematic representation showing preparation of targeted polymeric assemblies of invention from polymer-drug conjugates of formula I.

Two solutions were prepared to obtain targeted and non-targeted assemblies. For the formation of non-targeted assemblies 2.3 mg POEGMEMA-b-PCombMA block copolymer was dissolved in 500 µL THF in a glass vial and 3 mL water was added to this solution. THF in the vials was then evaporated at room temperature for 24 h. at open atmosphere to give micelles. Targeted assemblies were prepared in the same manner using cRGDfK-POEGMEMA-b-PCombMA and POEGMEMA-b-PCombMA mixture (1/5, w/w). A schematic representation of the preparation of non-targeted and targeted assemblies are provided in FIG. 2 and FIG. 3.

Example 1G: Critical Micelle Concentration (CMC) Measurements

The fluorescence probe method was utilized for the determination of CMC values of targeted and non-targeted assemblies. Block copolymer solutions (450 µL) were prepared in THF using serial dilution in vials as above. 50 µE solution of Nile Red in THF (0.03 mg/mL) and then 3 mL water was added to each vial. THF was evaporated completely at open atmosphere and final concentration values for 16 samples ranging between $1 \times 10^{-9}$ and $1 \times 10^{-5}$ M in 3 mL water were obtained. Fluorescence measurements were recorded by fluorescence spectrophotometer at an excitation wavelength of 550 nm and the emission was monitored from 580 to 660 nm.

For the determination of the minimum required concentration of the amphiphilic polymers to form the micelle type polymeric structures via self-assembly, the CMC values of the block copolymers were calculated by tracking the fluorescence intensity of Nile Red as function of polymer concentration.

Figure 4:
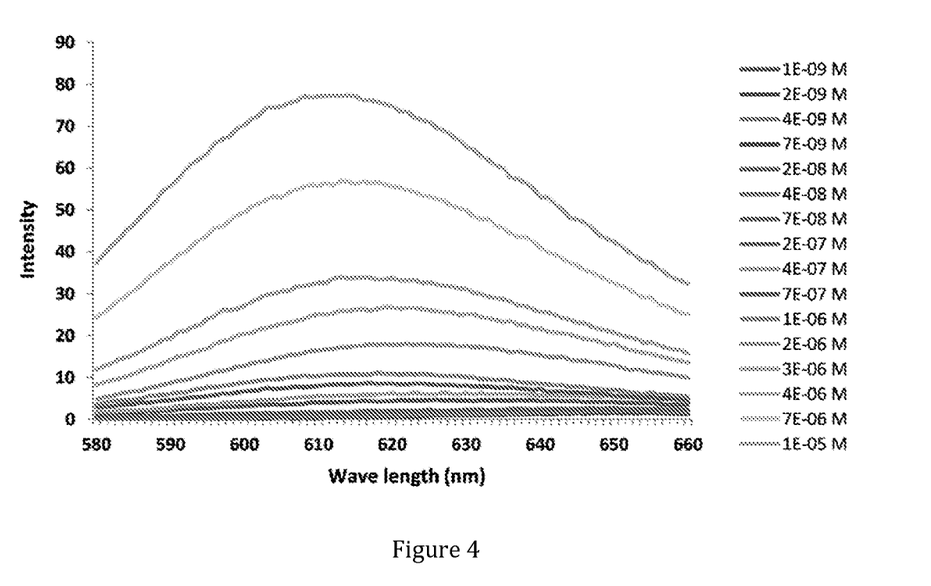
FIG. 4: Fluorescence emission spectra of Nile Red in non-targeted polymeric assemblies of invention.
Figure 5:
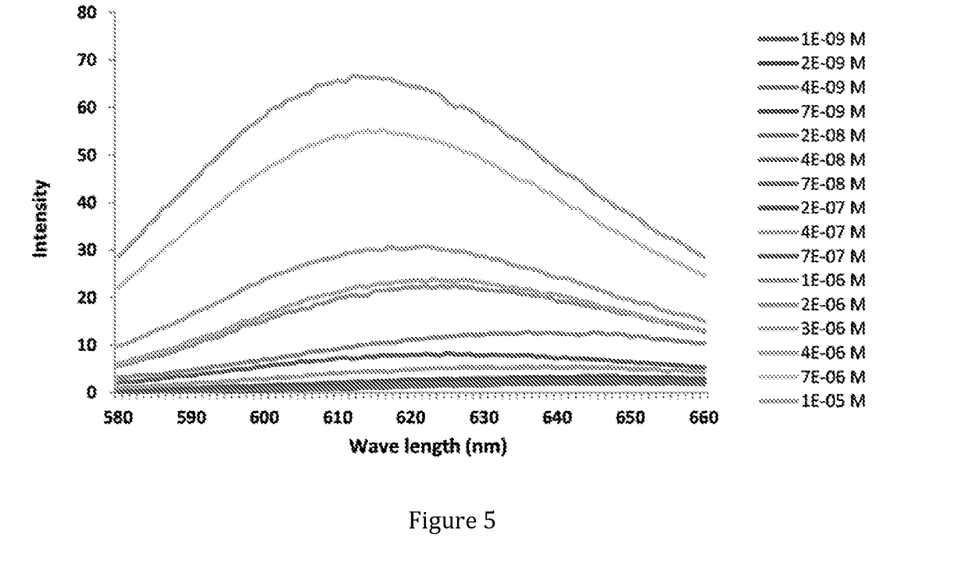
FIG. 5: Fluorescence emission spectra of Nile Red in targeted polymeric assemblies of invention.

Fluorescence emission spectra of Nile Red in non-targeted and targeted assemblies were obtained at an excitation wavelength of 550 nm and the emission monitored from 580 to 660 nm (FIG. 4 and FIG. 5 respectively)

Figure 6:
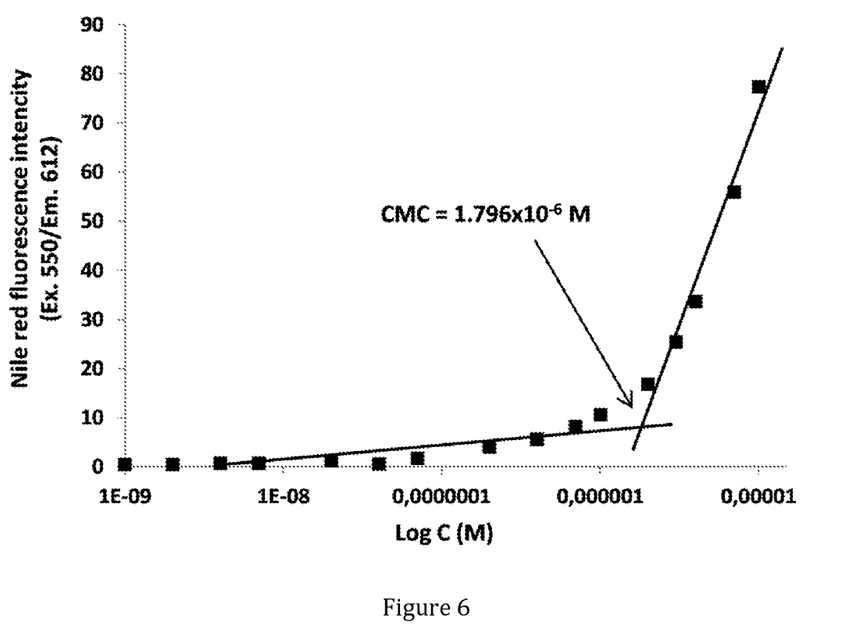
FIG. 6: Plot of the emission intensity at 612 nm versus the log of POEGMEMA-b-PCombMA concentration
Figure 7:
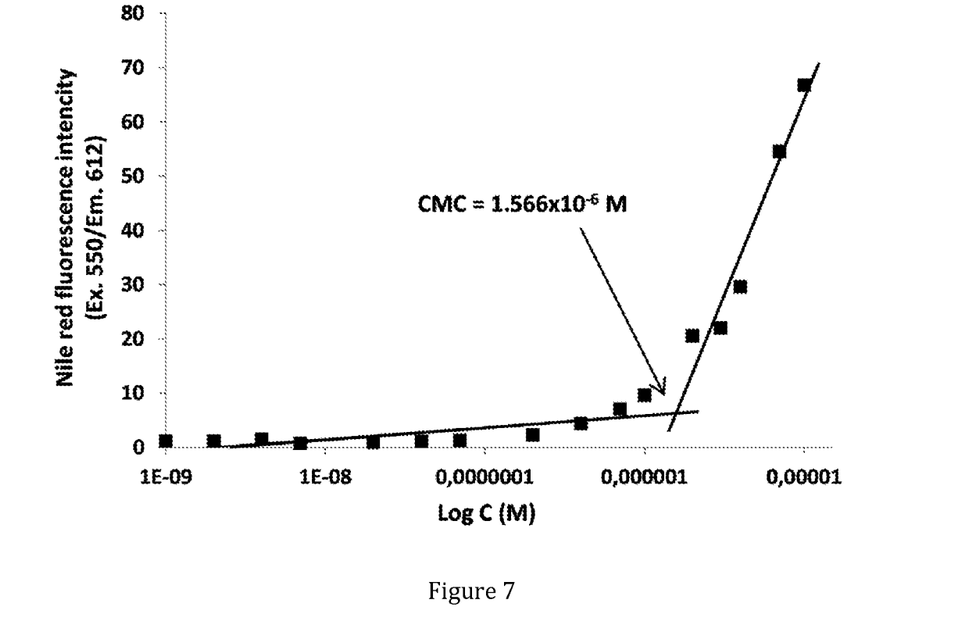
FIG. 7: Plot of the emission intensity at 612 nm versus the log of total POEGMEMA-b-PCombMA and cRGDfK-POEGMEMA-b-PCombMA concentration

For the determination CMC values, plots of the emission intensity at 612 nm versus the log of copolymer concentration were obtained. The CMC values for the non-targeted and targeted assembly formation were calculated by the intersection of the trendlines belonging to intensity ratios with relatively constant values and the rapidly increased intensity ratios (FIG. 6 and FIG. 7 respectively). The CMC values for non-targeted and targeted assembly formation was found to be $1.796 \times 10^{-6}$ M and $1.566 \times 10^{-6}$ M, respectively.

Example 2A: Synthesis of Polymerizable 5FU Monomer (5FU-MA)

5-fluorouracil (250 mg, 1.92 mmol) and 37% formalin (244 µL) was reacted at 60° C. for 2 h.

Then the mixture was cooled down and lypholized completely to yield a viscous compound. As the second step, this product (315 mg, 1.97 mmol) was dissolved in anyhdrous acetonitrile (5.8 mL) and then triethylamine (422 µL, 3.03 mmol) was added into this solution. After cooling the reaction mixture down to 0° C., methacryloyl chloride (232 µL, 2.38 mmol) was added dropwise. The reaction was let to run for overnight at room temperature and then white precipitate was filtered out. All volatiles were evaporated under vacuo and then the crude was dissolved with dichloromethane (20 mL), followed by extraction with 1M HCl (2×10 mL), IM NaHCO$_3$ (10 mL) and brine (10 mL). After concentrating the organic part, product was isolated in pure form by column chromatography on silica, eluting with ethylacetate:hexane mixture (30:70 v/v). The product was obtained as a viscous colorless oil (305 mg, 68% yield).

Example 2B: Synthesis of POEGMEMA Homopolymer

Reversible addition-fragmentation chain transfer (RAFT) polymerization was used for the synthesis of POEGMEMA homopolymer. For the synthesis of POEGMEMA polymer, to a solution of OEGMA (500 mg, 1.66 mmol) and CPADB (11.97 mg, 42.85 µmol) in DMF (2.5 mL), was added AIBN (0.78 mg, 4.76 µmol). The mixture was purged with N$_2$ to remove 02 and polymerization was stirred for at 70° C. for 16 h. Polymerization was stopped by cooling and air exposure. POEGMEMA polymer was purified by precipitation in diethyl ether. The polymer precipitate was dried under vacuo to give 95 mg polymer with 19% yield.

Example 2C: Synthesis of POEGMEMA-Co-5FU-MA Block Copolymer

RAFT polymerization was used for the synthesis of POEGMEMA-b-PSFU-MA block copolymer. To a solution of 5FU-MA (17.9 mg, 78.6 µmol) and POEGMEMA polymer as macro chain transfer agent (40 mg, 3.93 µmol) in DMF (0.30 mL), was added AIBN (0.13 mg, 0.786 µmol). The mixture was purged with N$_2$ to remove O$_2$ and polymerization was stirred at 70° C. for 16 h. Polymerization was stopped by cooling and air exposure. The crude was precipitated in diethyl ether. The polymer precipitate was dried under vacuo to give 16 mg polymer with 28% yield).

Example 3A: Synthesis of Polymerizable Combretastatin-A4 Monomer (Comb-ss-MA)

2-hydroxethyl methacrylate (500 mg, 3.8 mmol), 4,4'-dithiodibutyric acid (1.83 g, 7.6 mmol), N,N'-dicyclohexylcarbodiimide (1.59 mg, 7.8 mmol), 4-(Dimethylamino)pyridine (281 mg, 2.3 mmol) were dissolved in anhydrous dichloromethane (DCM) (54 mL) under N$_2$ in a 100 mL round bottom flask. Reaction was stirred for 16 h at room temperature. The crude was precipitated in cold diethyl ether and was left for 20 min under −20° C. The product was purified by using column chromatography on silica with ethyl acetate and hexane (20:80 v/v) (426 mg, 32% yield).

Then, the obtained product (300 mg, 0.85 mmol) and Combretastatin-A4 (270 mg, 0.85 mmol) were dissolved in anhydrous dichloromethane (DCM) (6 mL) with DIPC (129 mg, 1.02 mmol) and DMAP (104 mg, 0.85 mmol) under N$_2$ in a 25 mL round bottom flask. Reaction was stirred for 16 h at room temperature. The Comb-ss-MA monomer was purified using column chromatography on silica with ethyl acetate and hexane (30:70 v/v). (195 mg, 35% yield).

Example 3B: Synthesis of POEGMEMA and Comb-ss-MA-POEGMEMA Homopolymers

Reversible addition-fragmentation chain transfer (RAFT) polymerization was used for the synthesis of POEGMEMA. For the synthesis of POEGMEMA polymer, to a solution of OEGMA (1.0 g, 3.3 mmol) and CPADB (36.88 mg, 0.133 mmol) in DMF (5 mL), was added ARM (2.17 mg, 0.0013 mmol). The mixture was purged with $N_2$ to remove 02 and polymerization was stirred for 16 h at 70° C. Polymerization was stopped by cooling and air exposure. POEGMEMA polymer was purified by precipitation in diethyl ether. The polymer precipitate was dried under vacuum to give 715 mg polymer with 69% yield.

Example 3C: Synthesis of POEGMEMA-Co-Comb-ss-MA Block Copolymer

RAFT polymerization was used for the synthesis of POEGMEMA-b-PComb-ss-MA block copolymer. Comb-ss-MA (80 mg, 0.20 mmol) and POEGMEMA polymer as macro chain transfer agent (134 mg, 0.020 mmol) in DMF (1.07 mL), was added AIBN (0.68 mg, 0.004 mmol). The mixture was purged with $N_2$ to remove 02 and polymerization was stirred at 65° C. Polymerization was stopped by cooling and air exposure. The crude was precipitated in diethyl ether. The polymer precipitate was dried under vacuum to give 98 mg of polymer with 65% yield.

The examples given above show that the invention is applicable to a range of different linkers such as disulfide and acetal and to different drug molecules such as combretastatin and 5-FU.

The invention claimed is:

1. A polymer-drug conjugate of formula I in the form of a block co-polymer for delivery of therapeutic agents Formula I wherein:
  $R_1$, $R_2$ and $R_3$ are independently selected from H or $-CH_3$;
  x is a natural number between 1-100;
  y is a natural number between 1-100;
  n is a natural number between 1-50;
  L is a cleavable linker;
  D is a therapeutic agent that is combretastatin or 5-Fluorouracil (5-FU) or gemcitabine or chloroquine or doxorubicine;
  A is an end group or A may be null; and
  B is an end group or B may be null,
wherein: (a) A is (i) an end group that is a fragment of a chain transfer agent (CTA), an initiator or a fragment of a CTA, or (ii) an initiator conjugated with a targeting moiety selected from the group consisting of antibodies, antibody fragments, and peptides, a fragment of a CTA or initiator having a reactive functional group selected from the group consisting of: acetal, hemiacetal, carboxylic acid, alcohol, amide, imide, anhydride, aryl halide, azo compound, diazo compound, hydrazine, azide, carbonate, chlorosilane, cyanide, ester, sulfate ester, phosphate ester, thiophosphate ester, isocyanate, isothiocyanate, thiocarbamate ester, and dithiocarbamate ester; (b) B is an end group that is a fragment of a chain transfer agent or initiator; and (c) the polymer-drug conjugate is made by a method comprising:
  polymerizing PEG (meth)acrylate monomer (formula II)

Formula II to provide a polymer of formula IIa:

Formula IIa (ii) reacting formula IIa with a (meth)acrylate-L-D monomer (formula IIIa)

Formula IIIa to give polymer-drug conjugate of formula I.

2. The polymer drug conjugate according to claim 1, wherein linker is selected from a group comprising a poly (ethylene glycol), an amino acid, poly (amino acid) and short peptides.

3. The polymer drug conjugate according to claim 1, wherein the linker is a $C_1$-$C_{10}$ hydrocarbon or $C_1$-$C_{10}$ substituted or hetero substituted hydrocarbon, which comprises a functional group that dissociates under physiological conditions, wherein said functional group is selected from the group consisting of: acetal, ester, imine, amide, disulfide, carbonate, hydrazine, and carbamate.

4. The polymer drug conjugate according to claim 1, wherein the linker is null.

5. A polymeric assembly comprising a polymer-drug conjugates of formula I of claim 1.

6. The polymeric assembly according to claim 5, encapsulating therapeutic agents other than those attached to the polymer-drug conjugate of formula I wherein said therapeutic agents is selected from a group consisting of: nucleoside analogs, antifolates, other metabolites, topoisomerase I inhibitors, anthracyclines, podophyllotoxins, taxanes, vinca alkaloids, alkylating agents, platinates, antihormones, radiopharmaceutics, monoclonal antibodies, tyrosine kinase inhibitors, mammalian target of rapamycin (mTOR) inhibitors, retinoids, immunomodulatory agents, and histonedeacetylase inhibitors.

7. A pharmaceutical composition comprising a polymer-drug conjugate of formula I according to claim 1.

8. A method for treating cancer, the method comprising administering to a subject in need thereof the polymer-drug conjugate of formula I according to claim 1.

9. A method of treating cancer, the method comprising administering to a subject in need thereof the polymer-drug conjugate of formula I according to claim 1.

10. The polymeric assembly of claim 5, wherein the polymeric assembly are nanoparticles or miscelles.

11. The polymer drug conjugate according to claim 1, wherein the peptide is Cyclo (Arg-Gly-Asp-D-Phe-Lys) (cRGDfK) (SEQ ID No: 3).

12. The polymer drug conjugate of claim 3, wherein the reactive functional group is the reactive group is selected from the group consisting of acetal, hemiacetal, carboxylic acid, alcohol, amide, imide, anhydride, aryl halide, azo compound, diazo compound, hydrazine, azide, carbonate, chlorosilane, cyanide, ester, sulfate ester, phosphate ester, thiophosphate ester, isocyanate, isothiocyanate, thiocarbamate ester, and dithiocarbamate ester.

13. The polymer drug conjugate according to claim 2, wherein the short peptide is cathepsin B labile.

14. The polymer drug conjugate according to claim 2, wherein the short peptide is selected from a group consisting of Gly-Phe-Leu-Gly (SEQ ID NO: 1), Val-Cit, Phe-Lys, Val-Ala, and Ala-Leu-Ala-Leu (SEQ ID NO: 2).

* * * * *